(12) United States Patent
Dziedzic et al.

(10) Patent No.: US 8,512,343 B2
(45) Date of Patent: Aug. 20, 2013

(54) METHODS AND INSTRUMENTS FOR APPROXIMATING MISALIGNED VERTEBRA

(75) Inventors: Sara Dziedzic, Dorchester, MA (US); William J. Frasier, New Bedford, MA (US); Michael Mahoney, Middletown, RI (US); Nicholas Pavento, Marlboro, MA (US); Christopher L. Ramsay, West Wareham, MA (US); David Greg Anderson, Moorestown, NJ (US)

(73) Assignee: DePuy Synthes Products, LLC, Raynham, MA (US)

( * ) Notice: Subject to any disclaimer, the term of this patent is extended or adjusted under 35 U.S.C. 154(b) by 763 days.

(21) Appl. No.: 11/897,565

(22) Filed: Aug. 31, 2007

(65) Prior Publication Data

US 2009/0062858 A1     Mar. 5, 2009

(51) Int. Cl.
*A61B 17/70* (2006.01)

(52) U.S. Cl.
USPC ............................................. 606/86 A

(58) Field of Classification Search
USPC ........................................ 606/86 A, 246–279
See application file for complete search history.

(56) References Cited

U.S. PATENT DOCUMENTS

| | | | |
|---|---|---|---|
| 4,653,481 A | 3/1987 | Howland et al. | |
| 5,306,275 A | 4/1994 | Bryan | |
| 5,439,377 A * | 8/1995 | Milanovich | 433/7 |
| 5,474,551 A | 12/1995 | Finn et al. | |
| 5,584,834 A | 12/1996 | Errico et al. | |
| 5,609,592 A | 3/1997 | Brumfield et al. | |
| 5,624,441 A | 4/1997 | Sherman et al. | |
| 5,984,922 A | 11/1999 | McKay | |
| 6,159,179 A | 12/2000 | Simonson | |
| 6,468,276 B1 | 10/2002 | McKay | |
| 6,562,038 B1 | 5/2003 | Morrison | |
| 6,626,906 B1 | 9/2003 | Young | |
| 6,726,692 B2 | 4/2004 | Bette et al. | |
| 6,770,075 B2 | 8/2004 | Howland | |
| 6,916,330 B2 | 7/2005 | Simonson | |
| 6,929,606 B2 | 8/2005 | Ritland | |
| 6,951,538 B2 | 10/2005 | Ritland | |

(Continued)

FOREIGN PATENT DOCUMENTS

| | | |
|---|---|---|
| EP | 1339337 B1 | 9/2003 |
| EP | 1405606 A2 | 4/2004 |

(Continued)

OTHER PUBLICATIONS

Ebara, Sohei et al., "A New System for the Anterior Restoration and Fixation of Thoracic Spinal Deformities Using an Endoscopic Approach," *Spine*, vol. 25(7):876-883 (2000).

*Primary Examiner* — Mary Hoffman
*Assistant Examiner* — Tara Carter
(74) *Attorney, Agent, or Firm* — Nelson Mullins Riley & Scarborough LLP

(57) ABSTRACT

Methods and instruments are provided for connecting a rod extending along a patient's spinal column to a misaligned vertebra. The method comprises implanting a bone anchor in the misaligned vertebra, attaching an approximating device to the implanted bone anchor and rod, approximating the vertebra toward the rod using the approximating device, and connecting the rod to the bone anchor on the approximated vertebra. In certain embodiments the approximating device may include a winch mechanism. In other embodiments the approximating device is a cannula used in conjunction with a guide system.

3 Claims, 17 Drawing Sheets

(56) References Cited

U.S. PATENT DOCUMENTS

| | | |
|---|---|---|
| 6,964,665 B2 | 11/2005 | Thomas et al. |
| RE39,035 E | 3/2006 | Finn et al. |
| 7,008,431 B2 | 3/2006 | Simonson |
| 7,166,108 B2 | 1/2007 | Mazda et al. |
| 7,179,261 B2 | 2/2007 | Sicvol et al. |
| 7,527,638 B2 | 5/2009 | Anderson et al. |
| 7,666,188 B2 | 2/2010 | Anderson et al. |
| 7,951,175 B2 | 5/2011 | Chao et al. |
| 8,025,682 B2 | 9/2011 | Mahoney et al. |
| 8,057,518 B2 | 11/2011 | Frasier et al. |
| 8,075,591 B2 | 12/2011 | Ludwig et al. |
| 2004/0236330 A1 | 11/2004 | Purcell et al. |
| 2005/0040687 A1* | 2/2005 | Schuster et al. ........... 297/284.4 |
| 2005/0245928 A1* | 11/2005 | Colleran et al. ................ 606/61 |
| 2006/0089651 A1 | 4/2006 | Trudeau et al. |
| 2006/0111730 A1 | 5/2006 | Hay |
| 2006/0155278 A1 | 7/2006 | Warnick |
| 2006/0173456 A1 | 8/2006 | Hawkes et al. |
| 2006/0264934 A1 | 11/2006 | Fallin |
| 2006/0282074 A1 | 12/2006 | Renaud et al. |
| 2008/0077155 A1* | 3/2008 | Diederich et al. ............ 606/105 |
| 2009/0062822 A1 | 3/2009 | Frasier et al. |
| 2009/0062857 A1 | 3/2009 | Ramsay et al. |
| 2009/0062864 A1 | 3/2009 | Ludwig et al. |

FOREIGN PATENT DOCUMENTS

| | | |
|---|---|---|
| WO | WO-98/49961 A1 | 11/1998 |
| WO | WO-2004/080318 A1 | 9/2004 |
| WO | WO-2006/023514 A1 | 3/2006 |
| WO | WO-2006/047742 A2 | 5/2006 |
| WO | WO-2006/081375 A2 | 8/2006 |

* cited by examiner

METHODS AND INSTRUMENTS FOR APPROXIMATING MISALIGNED VERTEBRA

FIELD OF APPLICATION

The disclosed embodiments relate to a method and devices for use during spinal correction surgery. More particularly, the disclosed embodiments relate to manipulation of bone anchors as well as the vertebral body to which the bone anchor is attached.

BACKGROUND

Recently, the trend in spinal surgery has been moving toward providing minimally invasive devices and methods for implanting spinal fixation devices. One such method, for example, a rod-first method includes inserting spinal fixation element, such as a spinal rod, through a first incision and positioning the spinal fixation element along a patient's spinal column adjacent to one or more vertebra. After the spinal rod is inserted, one or more anchors are inserted each through a separate incision along the spinal rod. After an anchor is inserted and anchored in bone the anchor is coupled to the spinal rod. The rod-first method is a minimally invasive technique in which the anchors are inserted after the rod and adjacent to the rod, as opposed to a conventional surgical technique in which the anchors are inserted first then the rod is placed such that the rod lies over the anchors.

Unfortunately, in many instances one or more vertebra is out of alignment such that the vertebra is not immediately adjacent to the inserted spinal rod. In percutaneous or minimally invasive procedures, it is more difficult to move such misaligned vertebra so that the vertebra may be coupled to the spinal rod. Thus, there is a need for instruments and techniques to approximate a laterally displaced vertebra through a cannula or minimally invasive incision.

SUMMARY

Disclosed herein are instruments and methods for laterally translating vertebral bodies. The instruments and methods disclosed herein are particularly suited to facilitate approximation of a vertebra misaligned relative to a spinal rod and other vertebra to bring the vertebra inline with the rod and other vertebra.

In accordance with a one aspect, a method is provided for connecting a rod extending along a patient's spinal column to a vertebra misaligned to the central axis of a corrected spinal column. The method comprises implanting a bone anchor in the misaligned vertebra, attaching an approximating device to the implanted bone anchor and rod, approximating the vertebra toward the rod using the approximating device, and connecting the rod to the bone anchor on the approximated vertebra.

In accordance with another aspect, an instrument is provided for approximating a misaligned bone anchor toward a rod extending along a patient's spinal column. The instrument comprises a first clamp configured to attach to a first location on the spinal rod, a second clamp configured to attach a second location on the spinal rod, a bone anchor engagement portion disposed between the first and second clamps for engaging the misaligned bone anchor, and at least one winch mechanism connecting the first and second clamps to the bone engagement portion. In some embodiments, the winch mechanism is a rack and pinion mechanism. In other embodiments, the winch mechanism is a cable winch mechanism.

In accordance with another aspect, a system is provided for approximating a misaligned bone anchor toward a rod extending along a patient's spinal column. The system comprises a guide system and a cannula configured to engage the bone anchor and attach to the guide portion of the guide system. The guide system comprises a guide portion and a rod engaging member. The guide portion is adapted to be positioned outside a patient's body and to extend along a patient's spinal column. The rod-engaging member is mated to the guide portion and adapted to couple to the rod and to maintain the rod in a fixed position within the patient's body extending adjacent to a patient's spinal column. The cannula comprises a proximal end, a distal end and a lumen extending between the proximal end and the distal end.

In one embodiment, the cannula is attached to the guide portion of the guide system with a ratchet mechanism. In another embodiment, the cannula further comprises a pivot mechanism disposed at the distal end of the cannula for capturing the rod and bone anchor. In still other embodiments, the cannula further comprises a first half configured to engage the rod and a second half configured to engage the bone anchor wherein combining the first half with the second half forms the cannula and approximates the vertebra toward the rod.

BRIEF DESCRIPTION OF THE FIGURES

These and other features and advantages of the instruments and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

DETAILED DESCRIPTION OF THE INVENTION

Certain exemplary embodiments will now be described to provide an overall understanding of the principles of the structure, function, manufacture, and use of the instruments and methods disclosed herein. One or more examples of these embodiments are illustrated in the accompanying drawings. Those of ordinary skill in the art will understand that the instruments and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

As discussed above, the use of minimally invasive surgical techniques, such as a rod first spinal fixation technique, provides some additional challenges. The manipulation of the rod or vertebra to effect corrective spinal fixation is more difficult using such techniques. Thus, when a vertebra is misaligned from the central axis of a corrected spinal column or otherwise not inline with the other vertebra of a patient's spinal column, manipulating or approximating the misaligned vertebra and rod into proximity of each may require specific methodology and instruments.

Figure 1:
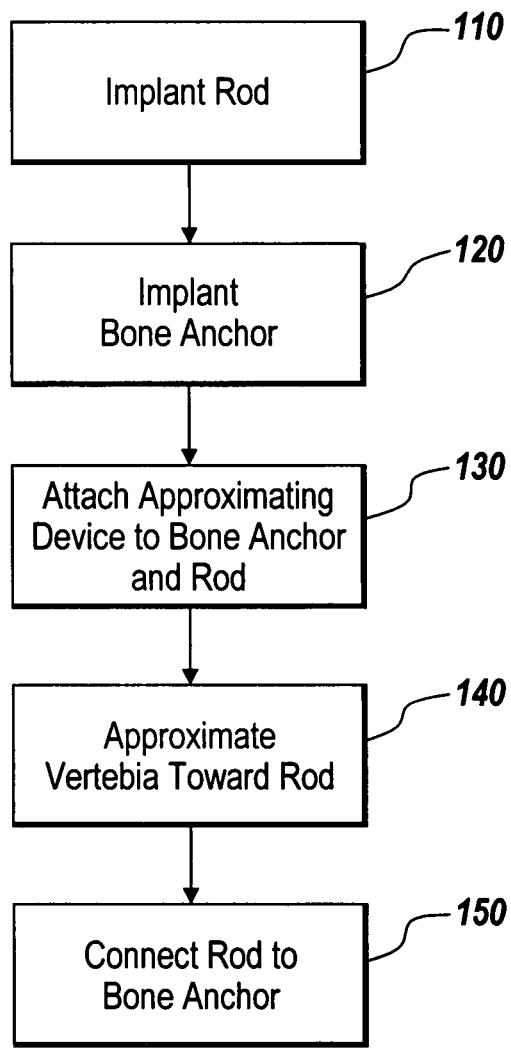
FIG. 1 is a flow chart of one exemplary method in for approximating a misaligned vertebra toward an implanted rod.

FIG. 1 illustrates a flow chart 100 of one exemplary method for connecting a rod to a misaligned vertebra. First, a rod is implanted along the patient's spinal column (step 110). A bone anchor is then implanted in the misaligned vertebra (step 120). An approximating device is then attached to the rod and bone anchor (step 130). The vertebra is then approximated toward the rod using the approximating device (step 140). Once, the vertebra and rod are in correct proximity, the rod is connected to the bone anchor (step 150). Each of these steps, including approximating devices used, is discussed in more detail below.

A variety of techniques can be used to implant a rod to extend along a patient's spinal column (step 110), and the rod can be introduced at various locations along the patient's spine. For example, the rod can be introduced through the same incision used to introduce a rod anchor system, or alternatively the rod can be introduced through an incision that is separate from and located a distance apart from the incision(s) used to implant the rod anchor system(s). The rod can also either be directly introduced through the incision to extend up along the patient's spinal column, or it can be introduced through a cannula, access port, or other device for guiding the rod to extend along the patient's spinal column. Various tools can also be coupled to the rod to manipulate and facilitate introduction and positioning of the rod in the patient's body. Once positioned, the rod may fixed by connecting the rod to one more bone anchors. The insertion, positioning and fixation of the rod along the spinal column is discussed in detail in the related applications: U.S. patent application Ser. No. 11/163,963, entitled "Minimally Invasive Spinal Fixation Guide System and Methods," filed on Nov. 4, 2005 and application DUQ-034 entitled "Minimally Invasive Guide System," filed on Aug. 31, 2007.

Figure 2A:
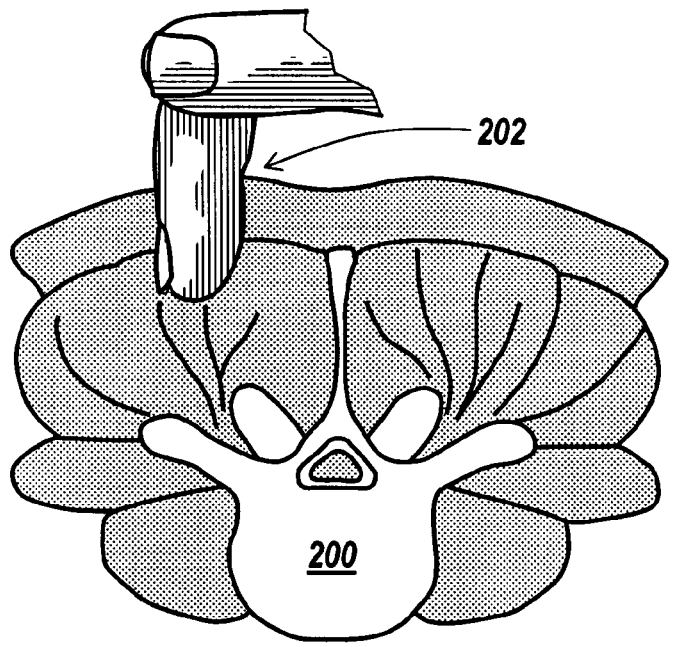
FIG. 2A is an end view showing a blunt dissection of the muscles surrounding a patient's vertebra.

Various techniques can be used to implant bone anchors, including the bone anchor in the misaligned vertebra 200; for example a minimally invasive percutaneous incision 202 may be made through the tissue at one or more of the sites. The location, shape, and size of the incision 202 will depend on the type and quantity of rod anchor systems being implanted, as well as the technique being employed to implant the rod anchor systems. In certain exemplary embodiments, one or more of the incisions may be expanded to create a pathway from the incision to proximate a vertebra 200. For example, the incision may be expanded by serial dilation, with a retractor such as an expandable retractor, or by any other conventional techniques. In one exemplary embodiment, blunt finger dissection can be used, as shown in FIG. 2A, to separate the longissimus thoracis and multifidus muscles, thereby exposing the facet and the junction of the transverse process and superior articular process.

Figure 2B:
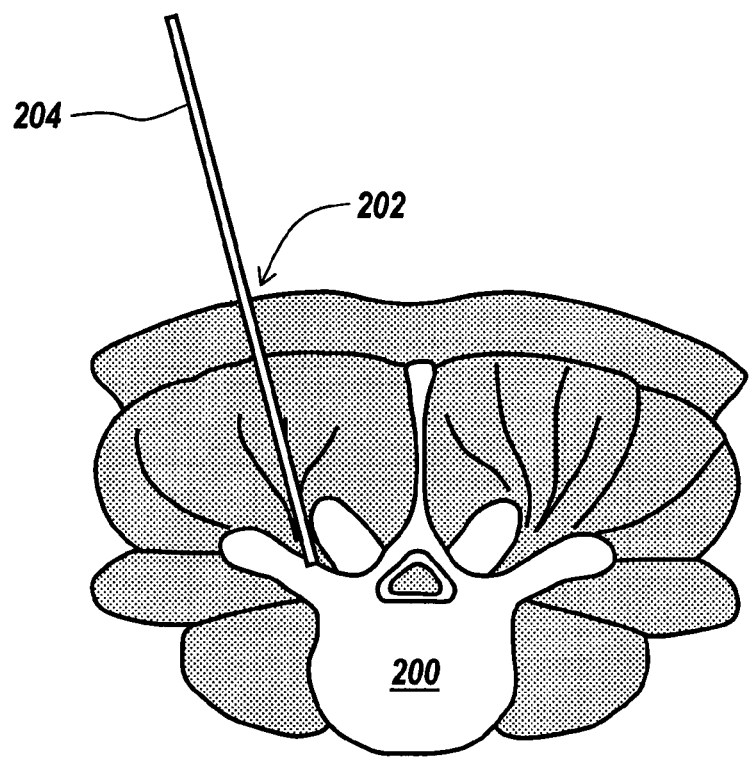
FIG. 2B is an end view of the vertebra in FIG. 2A with a k-wire placed through the incision and into the patient's vertebra.
Figure 2C:
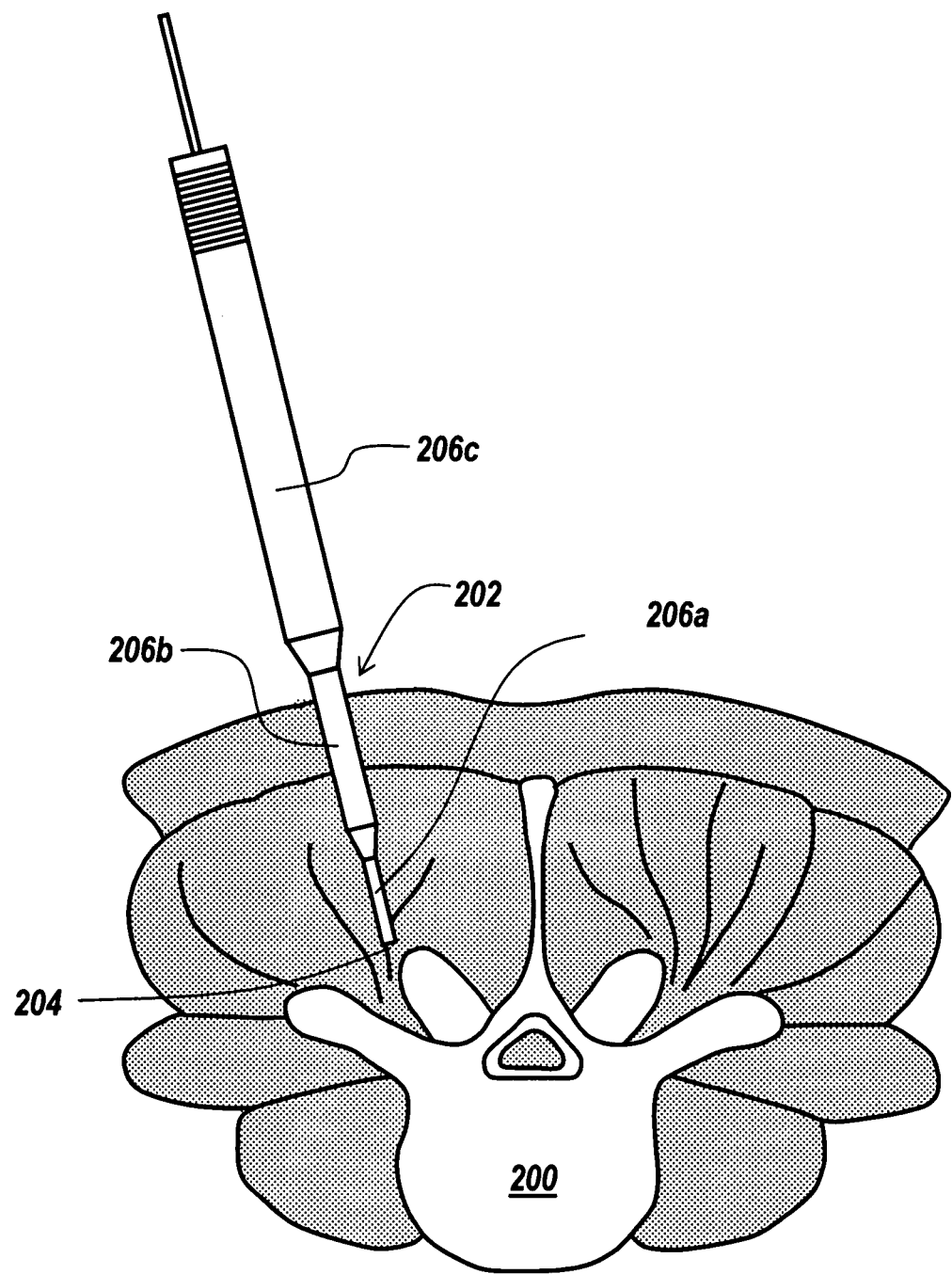
FIG. 2C is an end view of the vertebra in FIG. 2B showing an obturator and several dilators disposed over the k-wire to dilate the tissue and muscles.

A spinal anchor may be inserted through one or more of the incisions and the pathways to proximate the vertebra 200. Any technique for implanting a bone anchor can be used. In one embodiment, for example, a bone anchor can be implanted over a guidewire, such as a k-wire. As shown in FIG. 2B, a guide wire, e.g., a k-wire 204, can be implanted, either prior to or after formation of the incision, at each bone anchor implant site. The k-wire 204 may extend into the vertebra 200 at the desired entry point of the bone anchor. In certain exemplary embodiments, the k-wire 204 may be advanced into the vertebra 200. In other exemplary embodiments, the k-wire 204 may be positioned proximate to or against the vertebra 200. Fluoroscopy or other imaging may be used to facilitate proper placement of the k-wire 204. The incision may be dilated to provide a pathway for delivery of a bone anchor to each implant site, in the manner discussed above, before or after placement of the guidewire. For example, FIG. 2C illustrates serial dilation at one end of the incision 202 using an obturator 206a having several dilators 206b, 206c of increasing size placed there over. The dilators 206b, 206c are delivered over the obturator 206a and k-wire 204 to essentially stretch the skin around the incision 202 and to expand the pathway to the anchor site.

One skilled in the art will appreciate that a spinal anchor may be advanced to a vertebra 200 through the incision without the need for a guidewire 204.

Once the incision 202 is dilated to the proper size, if necessary, the vertebra 200 may be prepared using one or more bone preparation instruments, such as drills, taps, awls, burrs, probes, etc. In certain exemplary embodiments, one or more cannulae can be used to provide a pathway from the incision 202 to the anchor site for insertion of the bone preparation instruments and/or the anchor. In an exemplary embodiment, a relatively small cannula (not shown) may be used to introduce bone preparation instruments into the surgical site. Once the vertebra 200 is prepared, a bone anchor can be delivered along the k-wire, either through the cannula, or after the cannula is removed, and implanted in the vertebra 200. Alternatively, in embodiments not employing a guidewire, the bone anchor may be advanced through the incision, e.g., through a cannula, to the vertebra 200. A cannula, retractor, or other instrument may be employed to guide the bone anchor to the vertebra.

Figure 3:
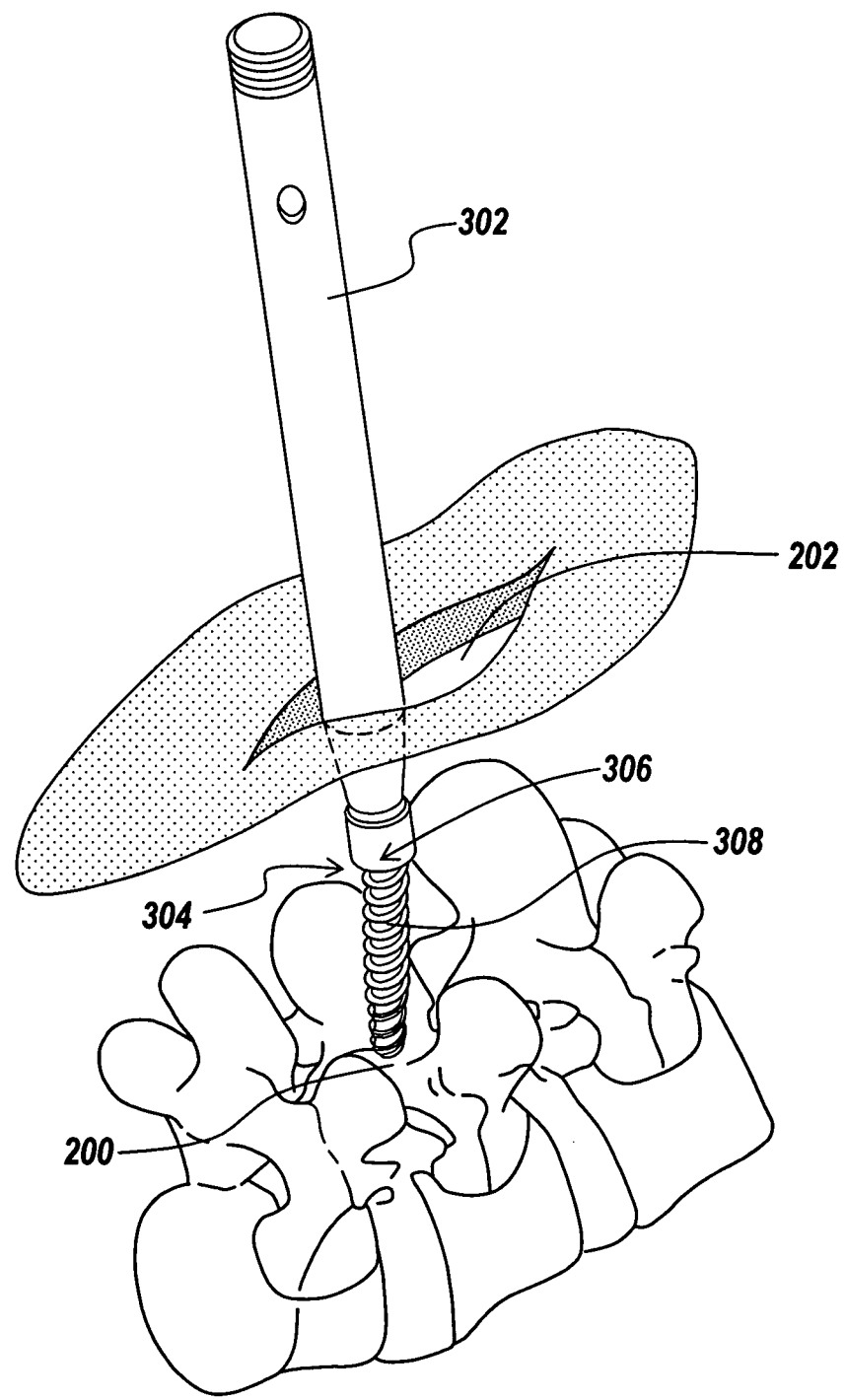
FIG. 3 is a perspective view of an insertion tool used to implant a bone anchor.

In another embodiment, shown in FIG. 3, a spinal anchor can be implanted in the vertebra using a minimally invasive technique. Such a procedure preferably begins by inserting a guidewire, such as a k-wire 204, through the incision and into the vertebra 200, dilating the incision to form a pathway, and preparing the vertebra 200, as discussed above. As shown in FIG. 3, a minimally invasive percutaneous access device 302, i.e., a cannula, is then inserted through the incision 202, preferably over the k-wire (not shown), to the target implant site on the vertebra 200. A bone anchor 304 can be attached to the distal end of the cannula 302, as shown, or the spinal anchor can be passed through the cannula 302 after the cannula 302 is positioned through the incision to extend to the target implant site. Once the bone anchor 304 is positioned adjacent to the vertebra 200, a driver tool (not shown) can be positioned through the access device 302 and coupled to a receiver head 306 of the bone anchor 304 to drive the bone anchor 304 into the vertebra 200.

This procedure, and other minimally invasive methods and devices for implanting a spinal anchor, are described in more detail in U.S. patent application Ser. No. 10/738,130 of Anderson et al. entitled "Methods And Devices For Minimally Invasive Spinal Fixation Element Placement," U.S. patent application Ser. No. 10/737,537 of Anderson et al. entitled "Methods And Devices For Spinal Fixation Element Placement," and U.S. patent application Ser. No. 10/738,286 filed on Dec. 16, 2003 and entitled "percutaneous access device and bone anchor assembly."

One skilled in the art will appreciate that a variety of anchor systems can be used with the techniques described herein. Examples of such systems are described in U.S. patent application Ser. No. 11/163,963, entitled "Minimally Invasive Spinal Fixation Guide System and Methods," filed on Nov. 4, 2005; DUQ-033 entitled "Adaptable Clamping Mechanism for Coupling a Spinal Fixation Element to a Bone Anchor," filed on Aug. 31, 2007; DUQ-036 entitled "Spanning Connector for Connecting a Spinal Fixation Element and an Offset Bone Anchor," filed on Aug. 31, 2007; and DUQ-37 entitled "Method and System for Securing a Rod to a Bone Anchor with a Connector," filed on Aug. 31, 2007.

This embodiment, and other methods for implanting spinal anchors using an access port, are described in more detail in U.S. Pat. No. 6,159,179 of Simonson entitled "Cannula And Sizing And Insertion Method," U.S. Publication No. 2003/0083689 of Simonson entitled "Non Cannulated Dilators," and U.S. Publication No. 2003/0083688 of Simonson entitled "Configured And Sized Cannula."

A person having ordinary skill in the art will appreciate that the aforementioned methods for implanting bone anchors can be modified depending on the type of anchor being implanted, as well as the specific procedure being employed. Moreover, other methods and devices known in the art can be used in accordance with the present invention. By way of non-limiting example, U.S. Patent Publication No. 2002/0123668 entitled "Retractor and Method for Spinal Pedicle Screw Placement," and U.S. Patent Publication No. 2003/0236447 entitled "Retractor and Method for Spinal Pedicle Screw Placement," each describe a surgical retractor and methods for spinal anchor placement which can be used with the present invention. These references are incorporated herein in their entirety.

Once the bone anchor has been implanted in the misaligned vertebra (step 120 of FIG. 1), an approximating device or instrument may be attached to the rod and/or bone anchor (step 130 of FIG. 1). Several embodiments of approximating devices and systems are discussed below.

In one embodiment, the approximating device involves a winch mechanism that is attached to the rod and bone anchor on the misaligned vertebra. Actuating the winch pulls the rod and misaligned vertebra together approximating the vertebra toward the rod (step 140 of FIG. 1). It should be understood that are many winch implementations and techniques that may be used. Some possible examples can be seen in FIGS. 4 and 5. Other possible embodiments will be apparent to one skilled in the art given the benefit of this disclosure.

Figure 4:
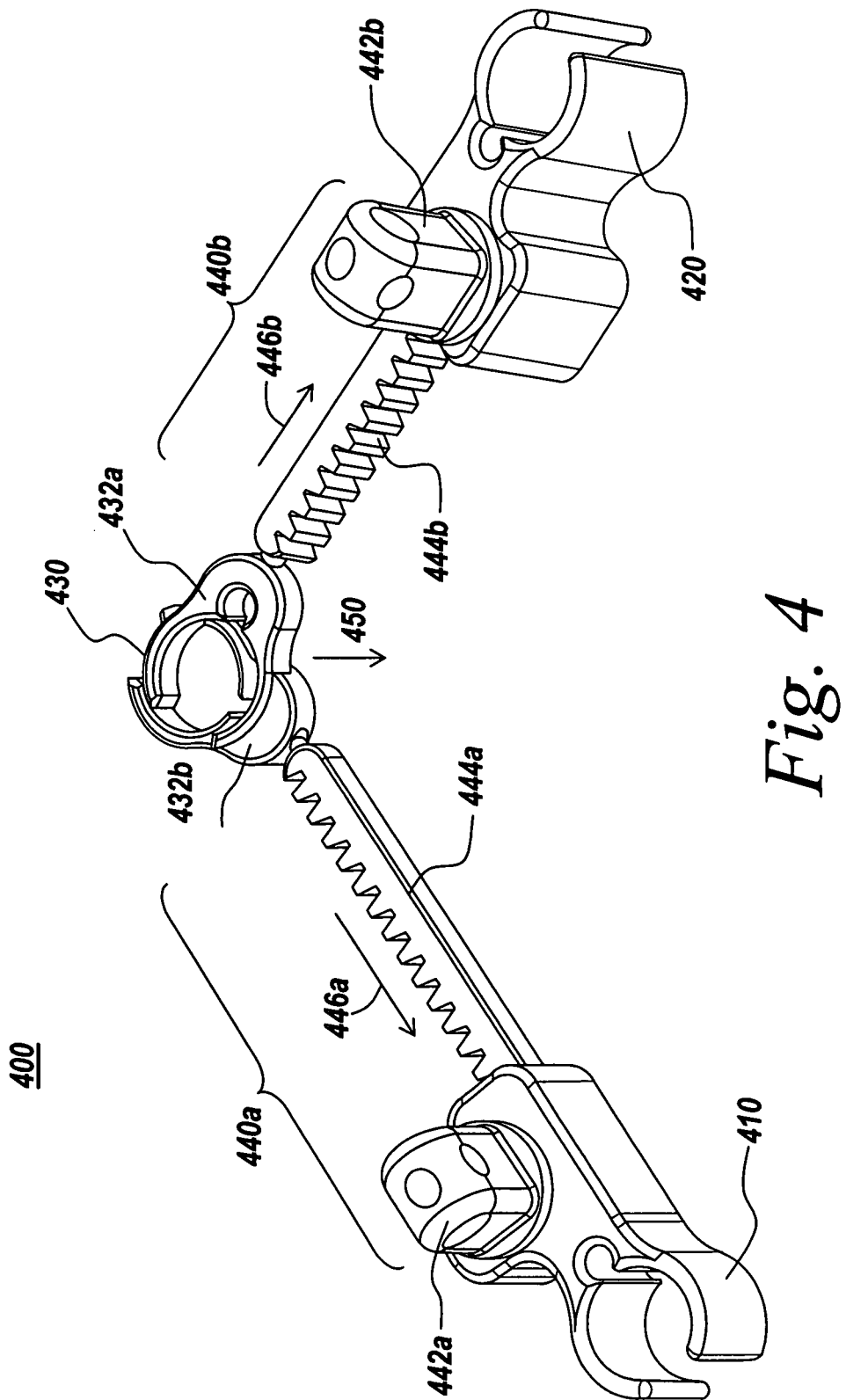
FIG. 4 is a perspective view of one exemplary embodiment of an approximating instrument using a winch mechanism.

FIG. 4 illustrates one embodiment of an approximating instrument 400 having a winch mechanism wherein the winch mechanism is a rack and pinion mechanism. In this example, the instrument 400 includes a first clamp 410, a second clamp 420, a bone anchor engagement portion 430, and at least one winch mechanism 440a, 440b. The first clamp 410 configured to attach to a first location. The second clamp 420 configured to attach a second location separated from the first location. The bone anchor engagement portion 430 is configured for engaging the bone anchor of the misaligned vertebra. The one or more winch mechanisms 440a, 440b are actuated to approximate the misaligned vertebra toward the rod.

In the present embodiment, the first clamp 410 and second clamp 420 are configured to attach to bone anchors connected to the rod. In use, the clamps 410, 420 are attached to bone anchors at the ends of the rod such that the misaligned vertebra is misaligned from a location on the rod between the location of the first and second clamps 410, 420. In other embodiments, the clamps 410, 420 may attach directly to the rod or to other instruments, devices, systems, or tools attached to the rod or a bone anchor.

The bone engagement portion 430 engages the bone anchor on the misaligned vertebra. In other embodiments, the bone engagement portion 430 may also be attached to instruments, devices, systems, or tools attached to a bone anchor. In the embodiment of FIG. 4, the bone anchor engagement portion 430 is disposed between the first clamp 410 and the second clamp 420. In this example the bone anchor engagement portion includes two yokes 432a, 432b for attaching to a bone anchor, each yoke 432a, 432b is connected to one of the clamps 410, 420 by a rack and pinion winch mechanism 440a, 440b. This allows yokes 432a, 432b to move independently when the vertebra is being approximated. In certain embodiments, the bone engagement portion 430 may also allow the bone anchor to rotate in relation to the clamps 410, 420.

In the embodiment of FIG. 4, the winch mechanisms 440a, 440b are rack and pinion winch mechanisms. Once the instrument 400 is in position and attached to the rod and bone anchor (not shown), the misaligned vertebra may be approximated toward the rod (step 140 of FIG. 1) by actuating the rack and pinion winch mechanisms 440a, 440b wherein the bone anchor (and the vertebra to which it is attached) are pulled toward the rod. To actuate the rack and pinion winch mechanisms 440a, 440b, the pinion 442a, 442b is turned. The pinion 442a, 442b engages the rack 446a, 446b pulling it in the direction indicated by arrows 446a, 446b respectively. This, in turn, pulls the bone anchor engagement portion 430 attached to the bone anchor on the misaligned vertebra (not shown) toward the rod (not shown) in the direction indicated by arrow 450. The individual winch mechanisms 440a, 440b may be actuated together or independently as needed to approximate the misaligned vertebra toward the rod as needed.

Figure 5:
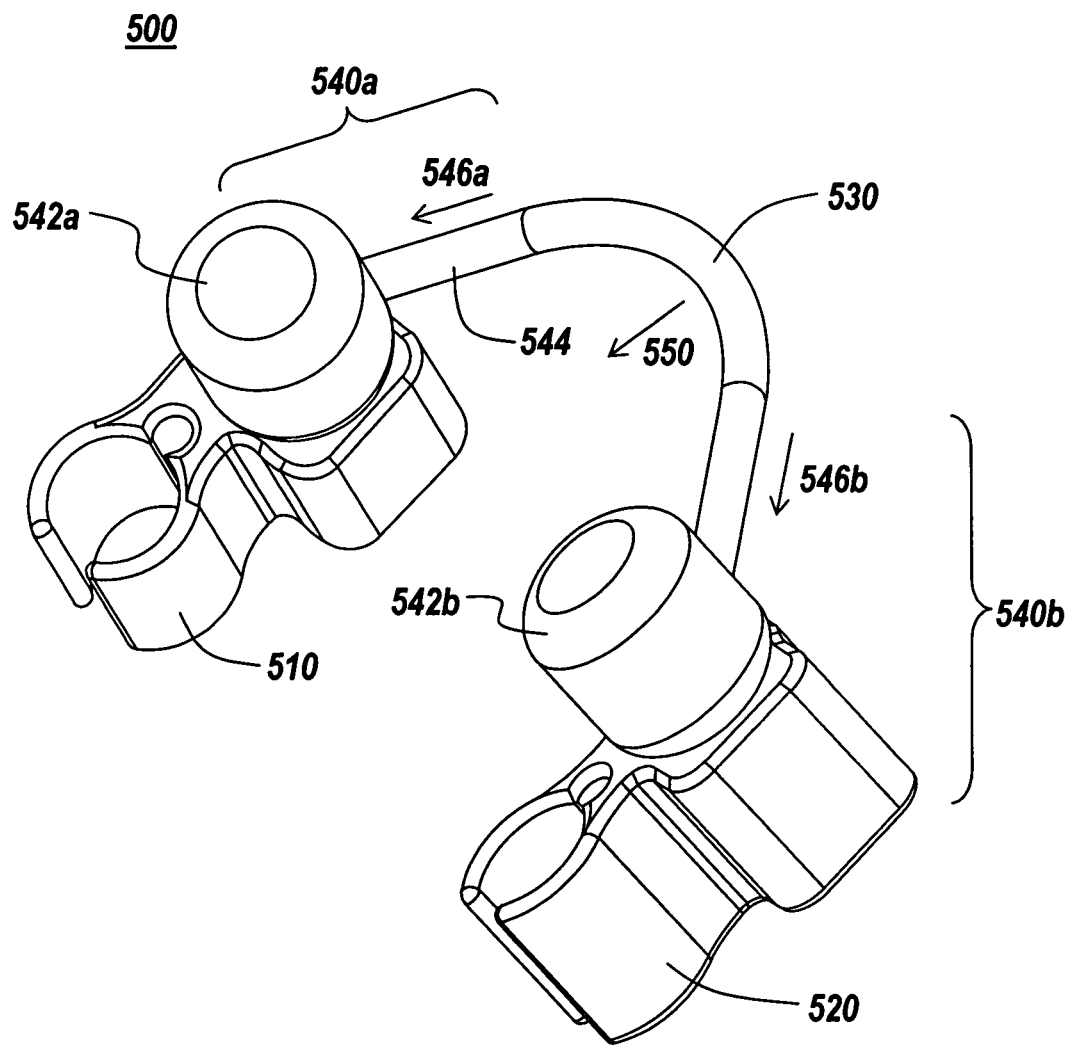
FIG. 5 is a perspective view of another exemplary embodiment of an approximating instrument using a winch mechanism.

FIG. 5 illustrates another embodiment of approximating instrument 500 having a winch mechanism wherein the winch mechanism is a cable winch mechanism. As with the example of FIG. 4, the instrument 500 of FIG. 5 includes a first clamp 510, a second clamp 520, a bone anchor engagement portion 530, and at least one winch mechanism 540a, 540b. The first clamp 510 configured to attach to a first location. The second clamp 520 configured to attach a second location separated from the first location. The bone anchor engagement portion 530 is configured for engaging the bone anchor of the misaligned vertebra. The one or more winch mechanisms 540a, 540b are actuated to approximate the misaligned vertebra toward the rod.

As in FIG. 4, the first clamp 510 and second clamp 520 are configured to attach to bone anchors connected to the rod. In use, the clamps 510, 520 are attached to bone anchors at the ends of the rod such that the misaligned vertebra is misaligned from a location on the rod between the location of the first and second clamps 510, 520. In other embodiments, the clamps 510, 520 may attach directly to the rod or to other instruments, devices, systems, or tools attached to the rod or a bone anchor.

The bone engagement portion 530 engages the bone anchor on the misaligned vertebra. In other embodiments, the bone engagement portion 530 may also engage instruments, devices, systems, or tools attached to a bone anchor. In the embodiment of FIG. 5, the bone anchor engagement portion 530 is disposed between the first clamp 510 and the second clamp 520. In this example the bone anchor engagement portion 530 includes is a portion of the cable 544 configured to be wrapped around or otherwise engage the bone anchor. In other embodiments the bone anchor engagement portion 530 may include a specifically configured engagement seat.

In the embodiment of FIG. 5, the winch mechanisms 540a, 540b are cable winch mechanisms. Once the instrument 500 is in position and attached to the rod and bone anchor (not shown), the misaligned vertebra may be approximated toward the rod (step 140 of FIG. 1) by actuating the cable winch mechanisms 540a, 540b wherein the bone anchor (and the vertebra to which it is attached) are pulled toward the rod. To actuate the cable winch mechanisms 540a, 540b, the knob 542a, 542b is turned. The cable 544, which is attached to the knobs 542a, 542b, is then wrapped around the knob 542a, 542b pulling the cable 544 in the direction indicated by arrows 546a, 546b respectively. This in turn pulls the bone anchor engagement portion 530 attached to the bone anchor on the misaligned vertebra (not shown) toward the rod (not shown) in the direction indicated by arrow 550. The individual winch mechanisms 540a, 540b may be actuated together or independently as need to approximate the misaligned vertebra toward the rod as needed.

While the previous examples dealt with multiple winch mechanism and multiple attachment point on the rod, it will be understood by one skilled in the art that one winch mechanism may be used with multiple attachment points on the rod or with a single attachment point on the rod.

Since the techniques and instruments discussed herein deal with minimally invasive surgical techniques, wherein the rod and bone anchor are inserted precutaneously, the instruments may be attached outside the patient. In many instances, the bone anchor or devices attached to the bone anchors (e.g. cannulas) extend out of the patient through the percutaneous incisions. In other embodiments a guide system may be used to attach the instruments for approximation. An example of such a guide system can bee seen in FIG. 6.

Figure 6:
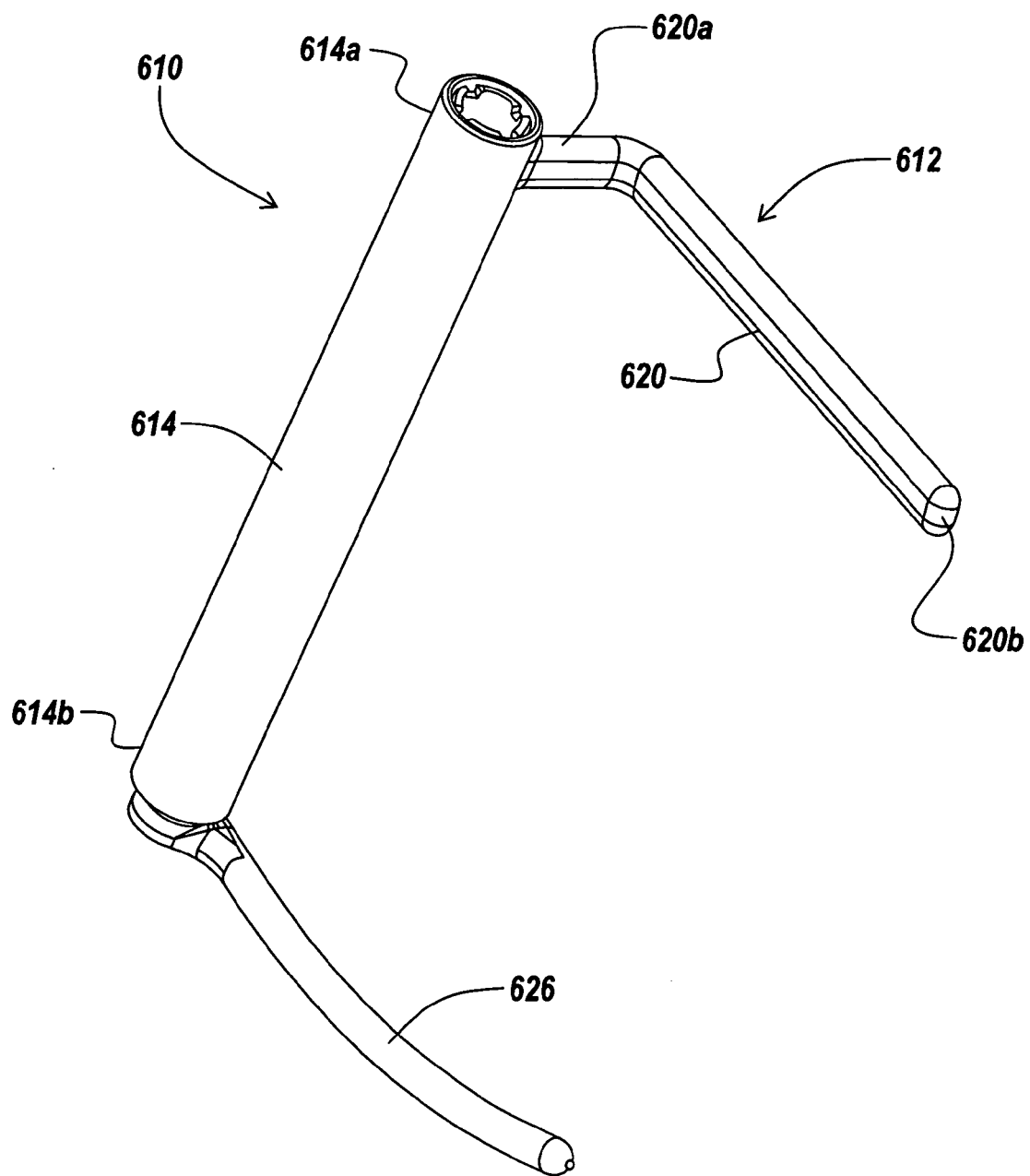
FIG. 6 is a perspective view of an guide system.

FIG. 6 illustrates an exemplary embodiment of a guide system 610 that can be used to target implant sites on one or more vertebra, facilitate implanting an anchor in a vertebra, and anchor approximating devices. As shown, the guide system 610 generally includes a guide portion 612 that is adapted to be positioned outside a patient's body and a rod-engaging portion 614 that is adapted to couple to a rod 626, to maintain the rod 626 in a fixed position within the patient's body such that the rod 626 extends adjacent to a patient's spinal column. The rod-engaging portion 614 may be effective to maintain the rod 626 in a position that is substantially parallel to, but spaced apart from, the guide portion 612 such that guide portion 612 serves as a guide located outside of the body to indicate the location of the rod 626 disposed inside the patient's body.

The guide portion 612 of the guide system 610 can have a variety of configurations. In one embodiment, for example, the guide system 610 is effective to indicate the position of a rod 626 disposed within and extending along a patient's spinal column. As shown in FIG. 6, the guide portion 612 has a generally elongate support rod 620 with opposed first and second ends 620a, 620b. The first end 620a may be adapted to couple to the rod-engaging portion 614. In the illustrated embodiment, the elongated support rod 620 is offset from the rod engaging portion 614 and rod 626 so that instruments and devices attached to the guide portion 612 are in line with the rod 626.

The rod-engaging portion 614 can have virtually any shape and size. For example, in the illustrated embodiment, the rod engaging portion 614 is a cannula that extends in a direction that is transverse to the support rod 620 and it is adapted to removably engage the rod 626. The first end 614a of the rod-engaging portion 614 may be mated to the first end 620a of the support rod 620, and the second end 614b of the rod-engaging portion 614 is in engagement with a rod 626. While not illustrated, virtually any technique can be used to removably engage a rod 626, including, for example, a clamping mechanism, a threaded engagement, an interference fit, etc. The rod-engaging portion 614 can also include a locking mechanism (not shown) for locking the rod 626 relative to the rod-engaging portion 614, and for subsequently releasing the rod 626 from the rod-engaging portion 614.

Further discussion of the guide system can be found in related U.S. patent application Ser. No. 11/163,963, entitled "Minimally Invasive Spinal Fixation Guide System and Methods," filed on Nov. 4, 2005, and DUQ-034 entitled "Minimally Invasive Guide System," filed Aug. 31, 2007.

Once the guide system 610 has been attached to a rod 626 using the rod engaging portion 614, the support rod 620 of the guide portion 612 provides a convenient place for attaching insertion and approximation devices. Examples of such instruments and devices can be seen in FIGS. 7-10.

As discussed above in regard to the implantation of the bone anchor in the misaligned vertebra, an insertion device, such as a cannula, is often used to insert a bone anchor. Since the cannula may engage the bone anchor at an implant site while extending outside the patient, it may be used to manipulate the bone anchor (i.e. approximating). It may also be conveniently attached to a guide system 610 which may be as an anchoring point for approximating the bone anchor towards the rod.

Figure 7A:
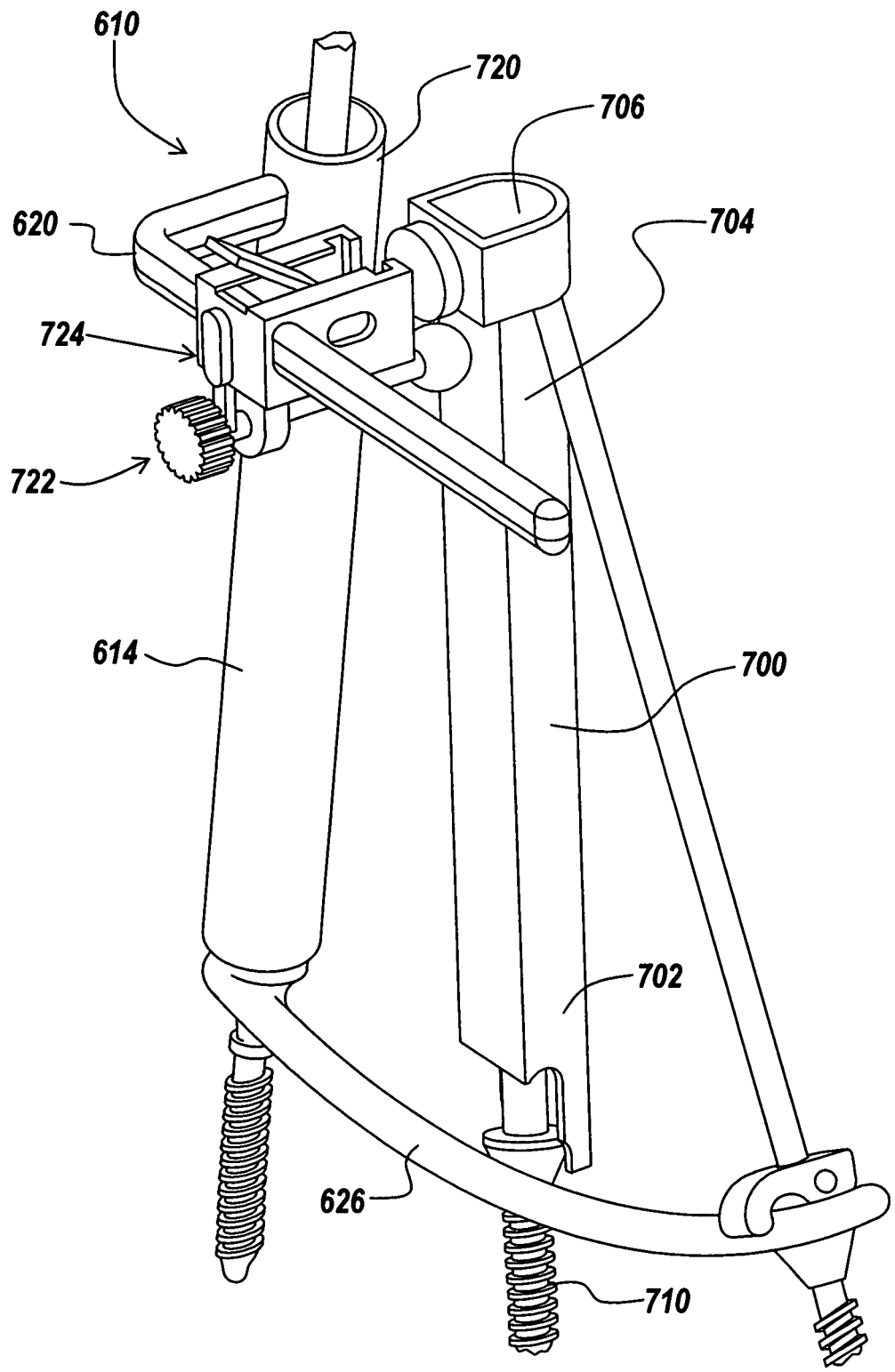
FIGS. 7A-7B depict one exemplary embodiment of an approximating system using a cannula.

FIG. 7A illustrates one embodiment of a cannula 700 used in connection with a guide system 610 to approximate a bone anchor 710 toward a rod 626. The cannula 700 has a distal end 702, a proximal end 704, and a lumen 706 extending therebetween. In this example, a bone anchor 710 has been inserted through the lumen 706. The cannula 700 is attached to the guide system 610 at the proximal end 704 using a ratchet mechanism 720. The guide system 610 has been attached to the rod 626 using the rod engagement portion 614 of the guide system.

The ratchet mechanism 720 is configured to slidably mount on the support arm 620 of the guide portion 612 of the guide system 610. The ratchet mechanism includes a ratchet 722 and a pawl 724. The pawl 724 is configured to engage the teeth of the ratchet 722 so as only allow movement in one direction (i.e. toward the rod).

Figure 7B:
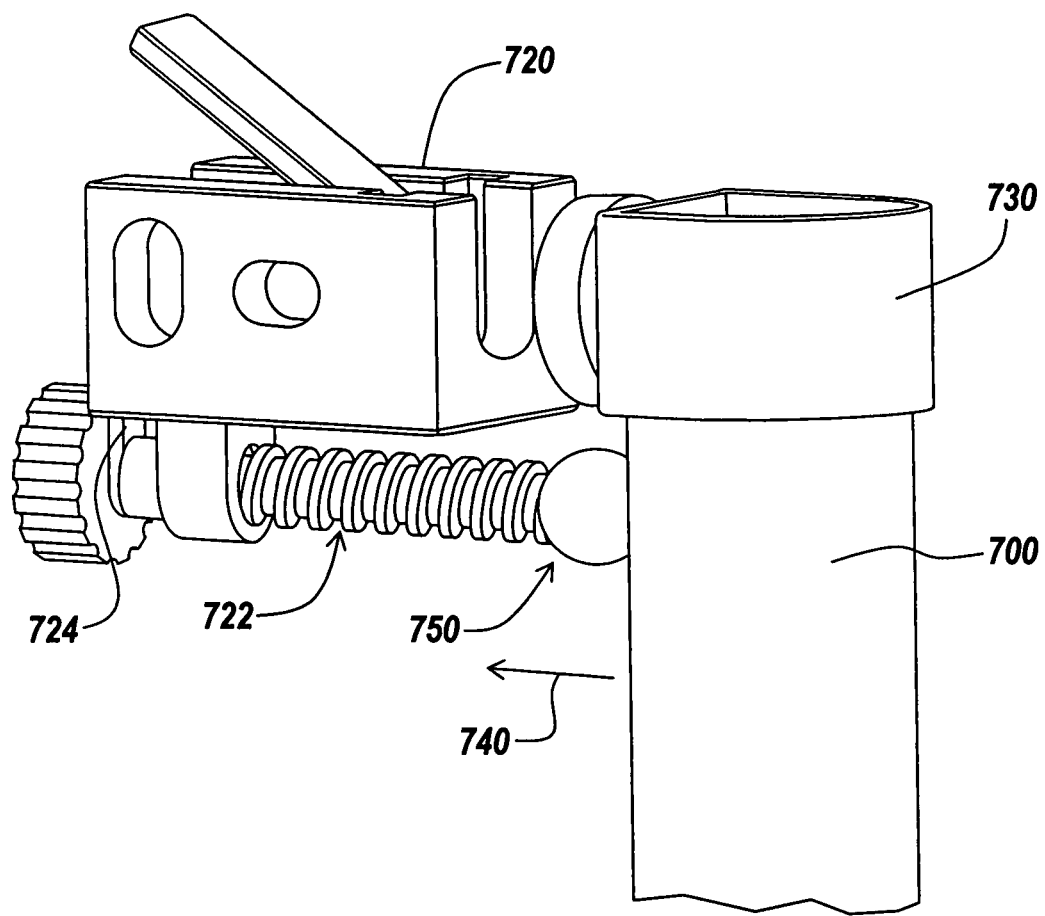

FIG. 7B provides a magnified view of the ratchet mechanism 720 for connecting the cannula 700 to the guide system 610 and approximating the bone anchor 710 toward the rod 626 (step 140 of FIG. 4). In this embodiment, the ratchet mechanism further includes a detachable sleeve 730 configured to hold a cannula 700. This configuration allows the cannula to be inserted first and then attached to the guide system 610. In certain embodiments the ratchet mechanism 720 further includes a poly-axial connection 750. The poly-axial connection allows the cannula to rotate or translate according to the placement of the bone anchor.

Once the cannula 700 is attached to the guide system 610, pulling on the ratchet 722 pulls the cannula in the direction indicated by arrow 740 (i.e. toward the rod). The ratchet may be move manually or mechanically. Since the cannula is engaging the bone anchor 710, the bone anchor 710 is also pulled in the direction indicated by arrow 740. The pawl 724 prevents the ratchet (as well as the cannula, bone anchor, and vertebra) from moving in the direction opposite that indicated by arrow 740. Thus, the misaligned vertebra is approximated toward the rod 626.

Figure 8A:
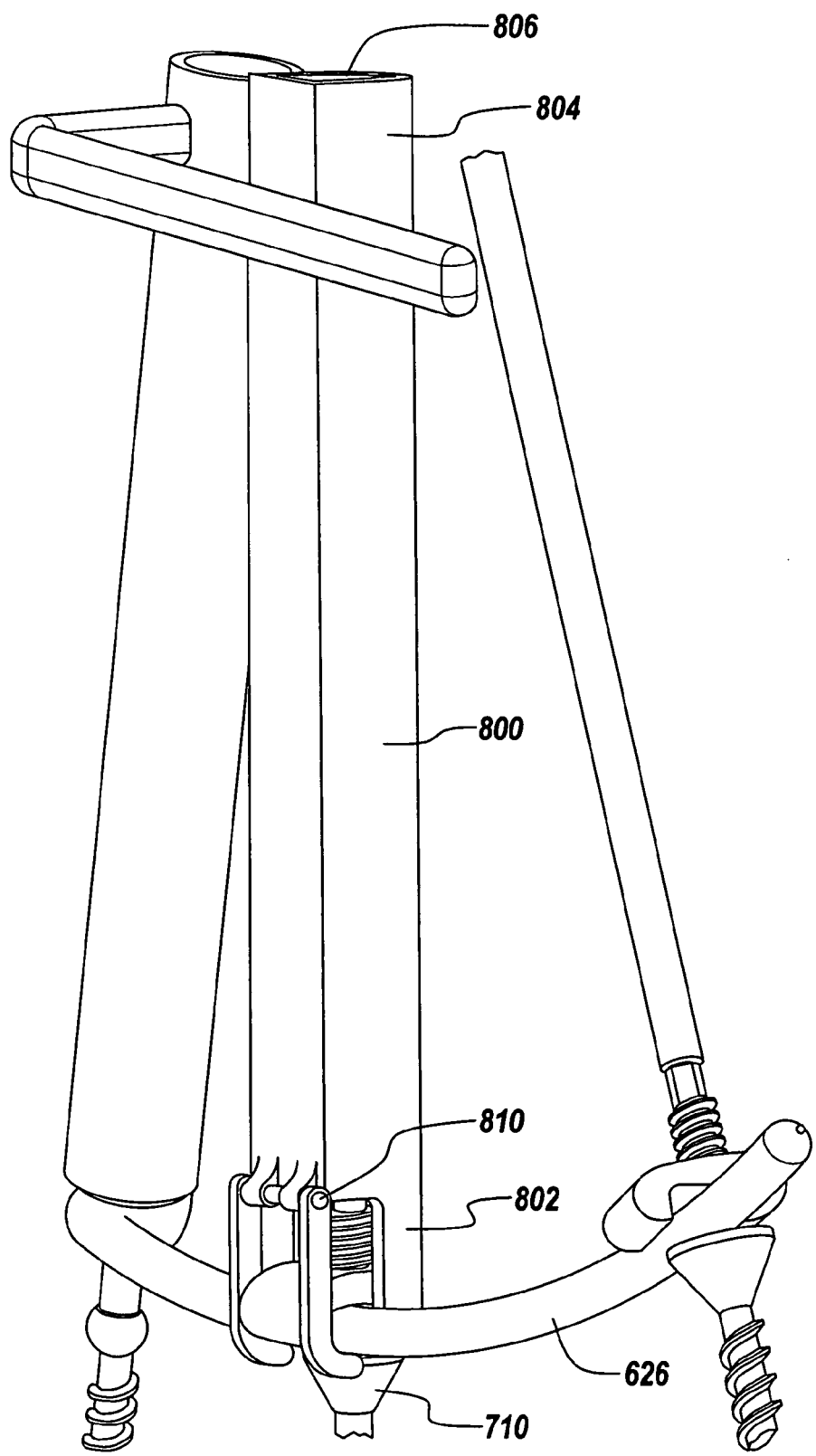
FIGS. 8A-8B depict another exemplary embodiment of an approximating system using a cannula.

FIG. 8A illustrates another embodiment of a cannula 800 used in connection with a guide system 610 to approximate a bone anchor 710 toward a rod 626. As with FIGS. 7A and 7B, the cannula 800 has a distal end 802, a proximal end 804, and a lumen 806 extending therebetween. In this embodiment, the cannula 800 further includes a pivot mechanism 810 a pivot mechanism at a distal end 802 of the cannula 800 for engaging the rod 626 and the bone anchor 710.

The pivot mechanism 810 can pivot away from the cannula to capture the rod 626. Moving the pivoting back towards the cannula 800 approximates the bone anchor 710 toward the rod 626 (step 140 of FIG. 4). Once the bone anchor 710 (and the attached vertebra) are in proximity to the rod 626 the pivot mechanism 810 may be locked to maintain the position of the bone anchor 710 and rod 626.

Figure 8B:
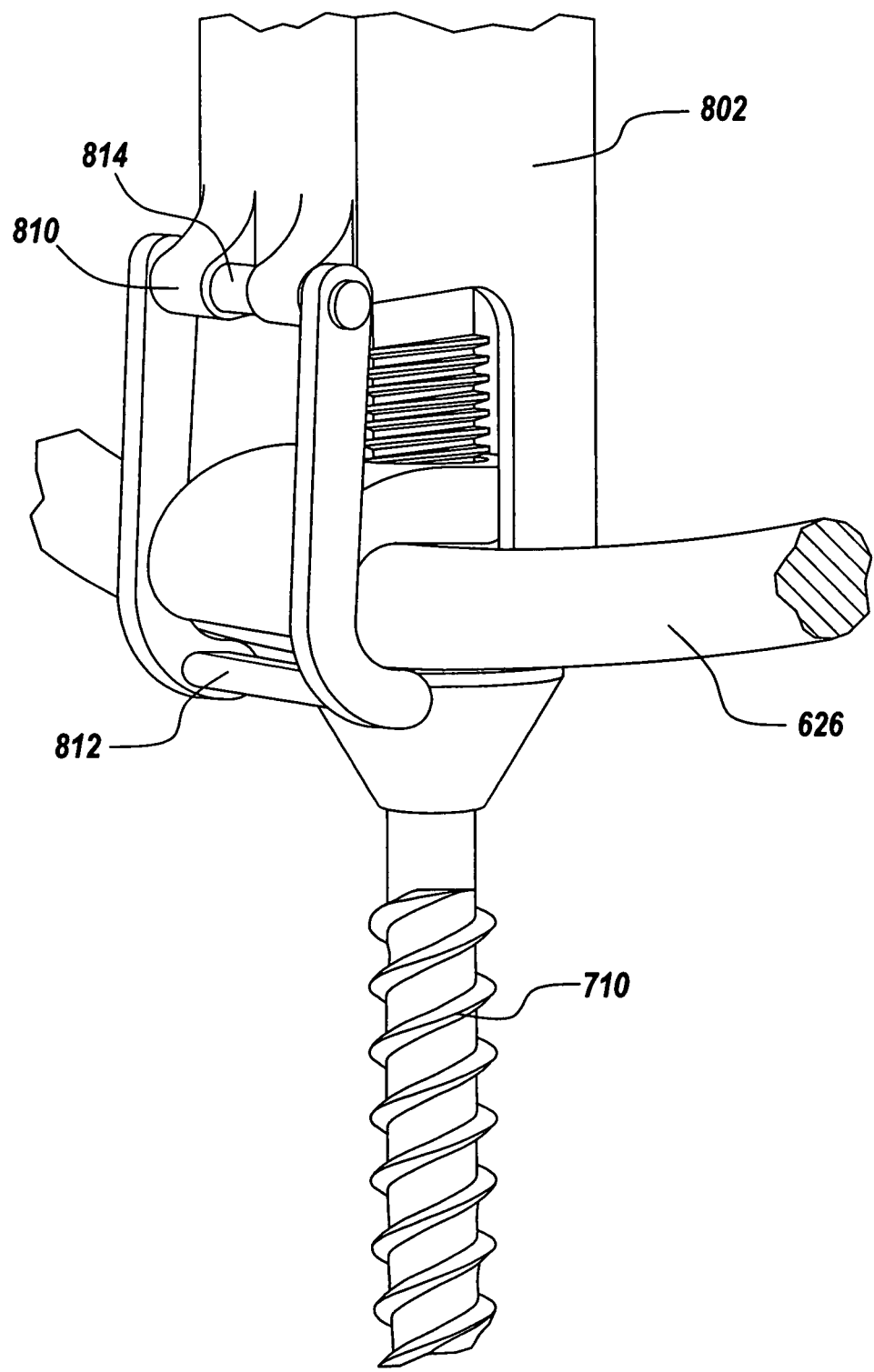

FIG. 8B provides a magnified view of the pivot mechanism 810 for engaging the rod 626 and bone anchor 710. In this embodiment, the pivot mechanism 810 further includes a clasp 812 for capturing the rod 626. The pivot mechanism 810 may be laser cut or a linkage. In certain embodiments the pivot mechanism 810 may be actuated from the proximal end 804 of the cannula 800 using an attached or secondary instrument. In the present example, a toothed pin 814 is provided that could be driven by an external gear or an internal linkage. Once the rod 626 and bone anchor have been captured and approximated by the clasp 812 of the pivot mechanism 810, their position may be locked using the pivot mechanism 810. In certain embodiments, a sleeve is slid over the cannula to lock the position of the rod 626 and bone anchor 710.

Figure 9A:
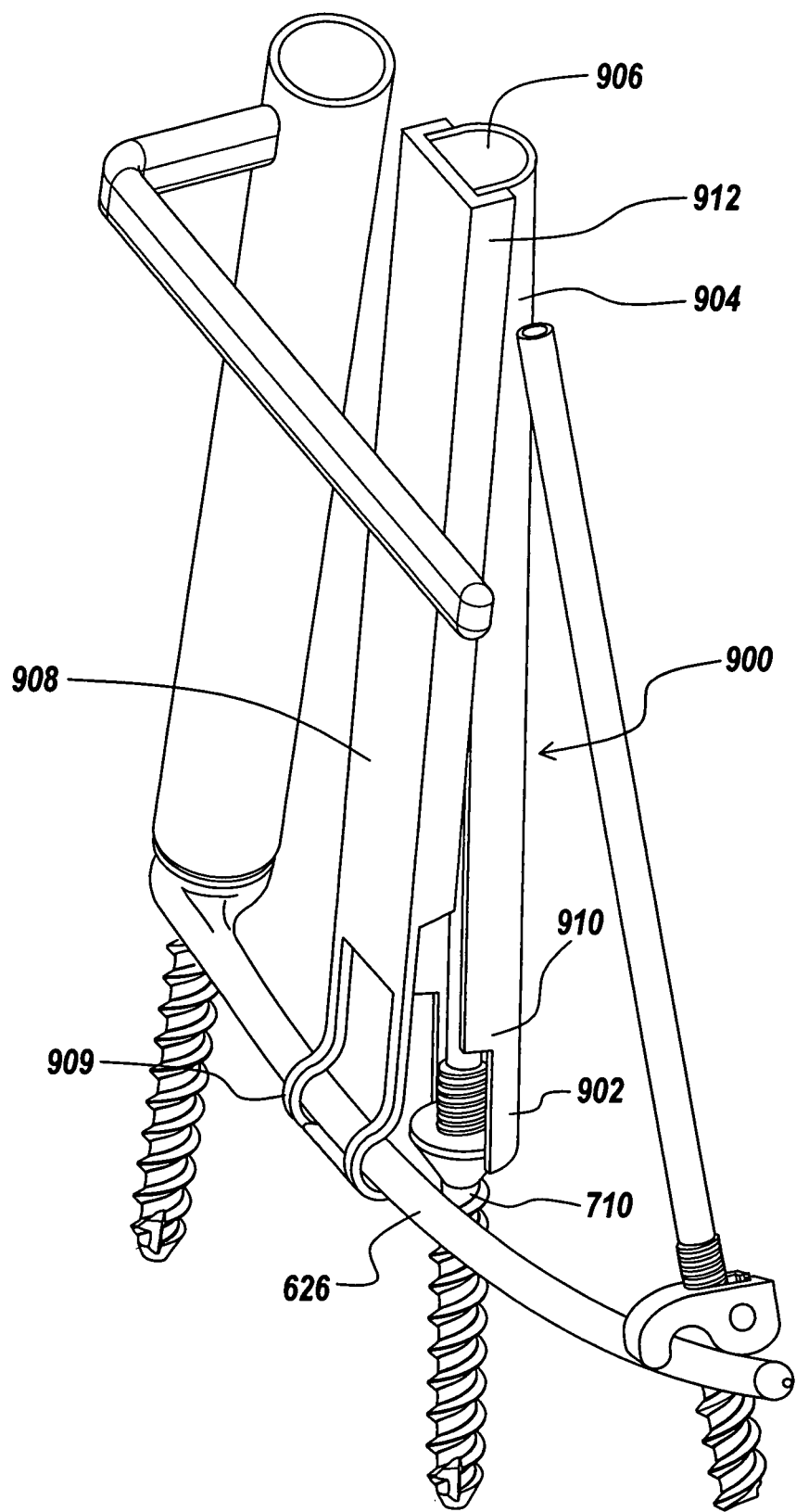
FIGS. 9A-9B depict another exemplary embodiment of an approximating system using a cannula.
Figure 9B:
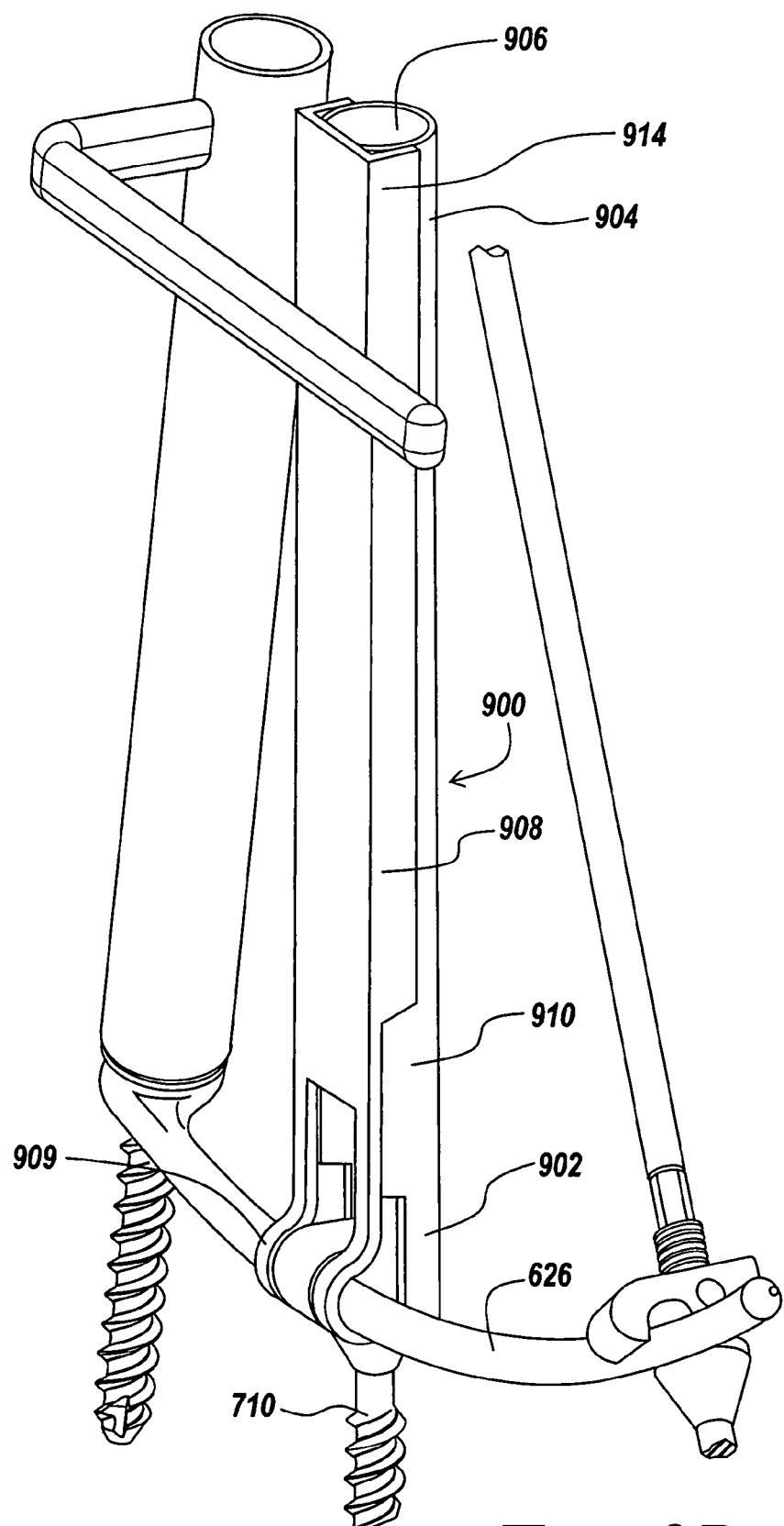

FIGS. 9A and 9B illustrate another embodiment of a cannula 900 used in connection with a guide system 610 to approximate a bone anchor 710 toward a rod 626. As with FIGS. 7A-8B, the cannula 900 has a distal end 902, a proximal end 904, and a lumen 906 extending therebetween. In this embodiment, the cannula 900 has two portions, in this case, halves. The first portion or half 908 is configured to engage the rod 626. The second portion or half 910 is configured to engage the bone anchor 710. Combining the first portion 908 and second portion 910 forms the cannula 900 and approximates the bone anchor 710 toward the rod 626.

In the embodiment of FIGS. 9A and 9B, the first portion 908 and second portion 910 are connected by a hinge 912 at the proximal end 904 of the cannula 900. In FIG. 9A, the first portion 908 is separated away from the second portion 910 in order to capture the rod 626 with configurations 909 on the first portion 908 adapted to engage the rod 626. In FIG. 9B, the first portion 908 has been combined with the second portion 910 through the use of sleeve 914 that presses the two portions 908, 910 together. Pressing the first portion 908 and second portion 910 together also moves the rod 626 and bone anchor 710 into proximity of each other. As such, the vertebra, which is attached to the bone anchor 710, is approximated toward the rod 626.

Although the previous examples have focused on lateral translation, it should be understood that the techniques and instruments discussed herein may also be used for rotation of bone anchors and vertebra. An example of this can be seen in FIGS. 10A-10D.

Figure 10A:
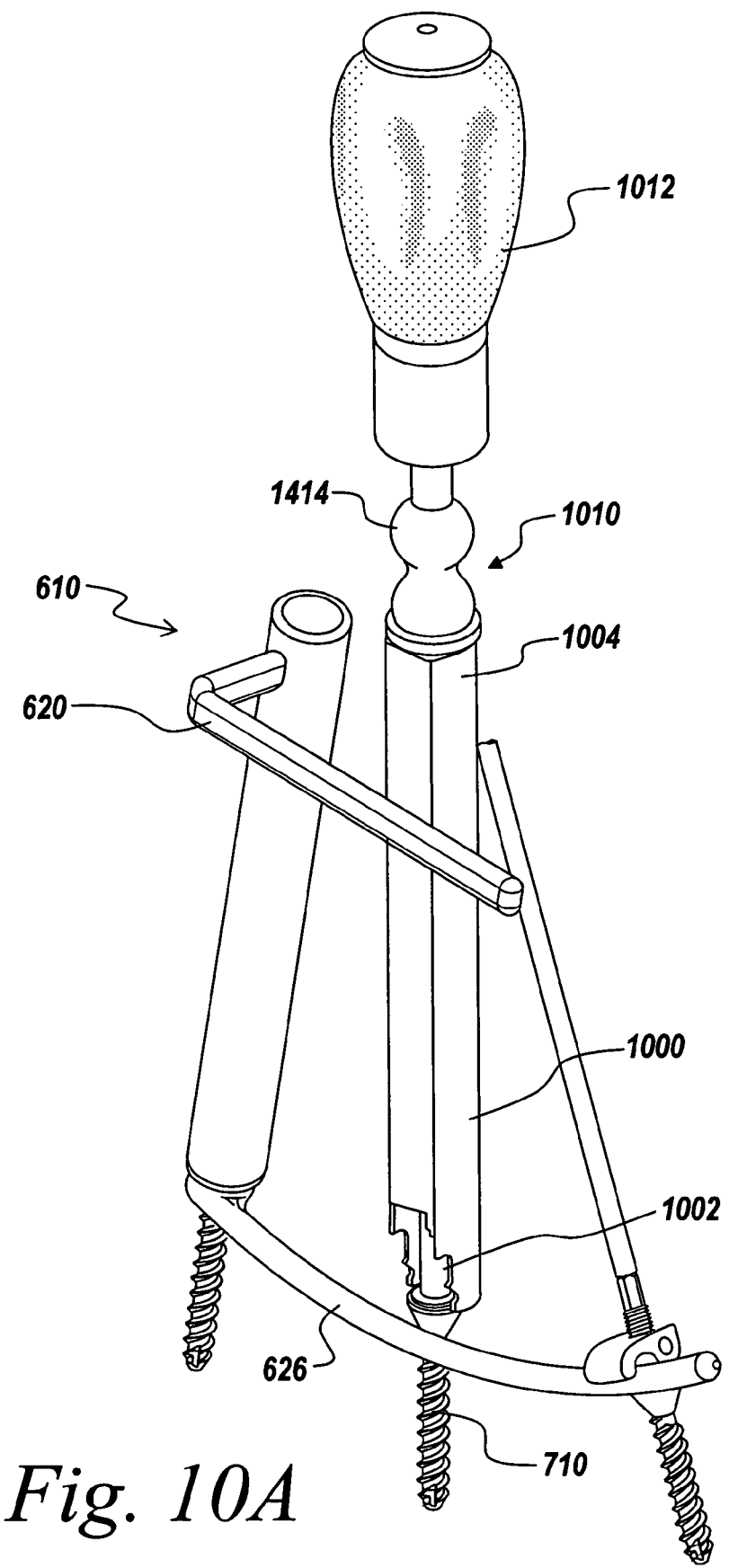
FIG. 10A-10D depict another exemplary embodiment of an approximating system using a cannula.

FIG. 10A illustrates one embodiment of a vertebral body rotator head 1010 that may be attached to a cannula 1000 such as discussed in relation to FIGS. 7-9. The vertebral body rotator head 1010 is configured to attach to the proximal end 1004 of the cannula 1000 allowing a surgeon to manipulate (i.e. rotate) the bone anchor 710 (and the vertebra attached) engaged at the distal end 1002 of the cannula 1000. In this example, the vertebral body rotator head has an attached handle 1012 to further assist in the rotation of the vertebra.

Figure 10B:
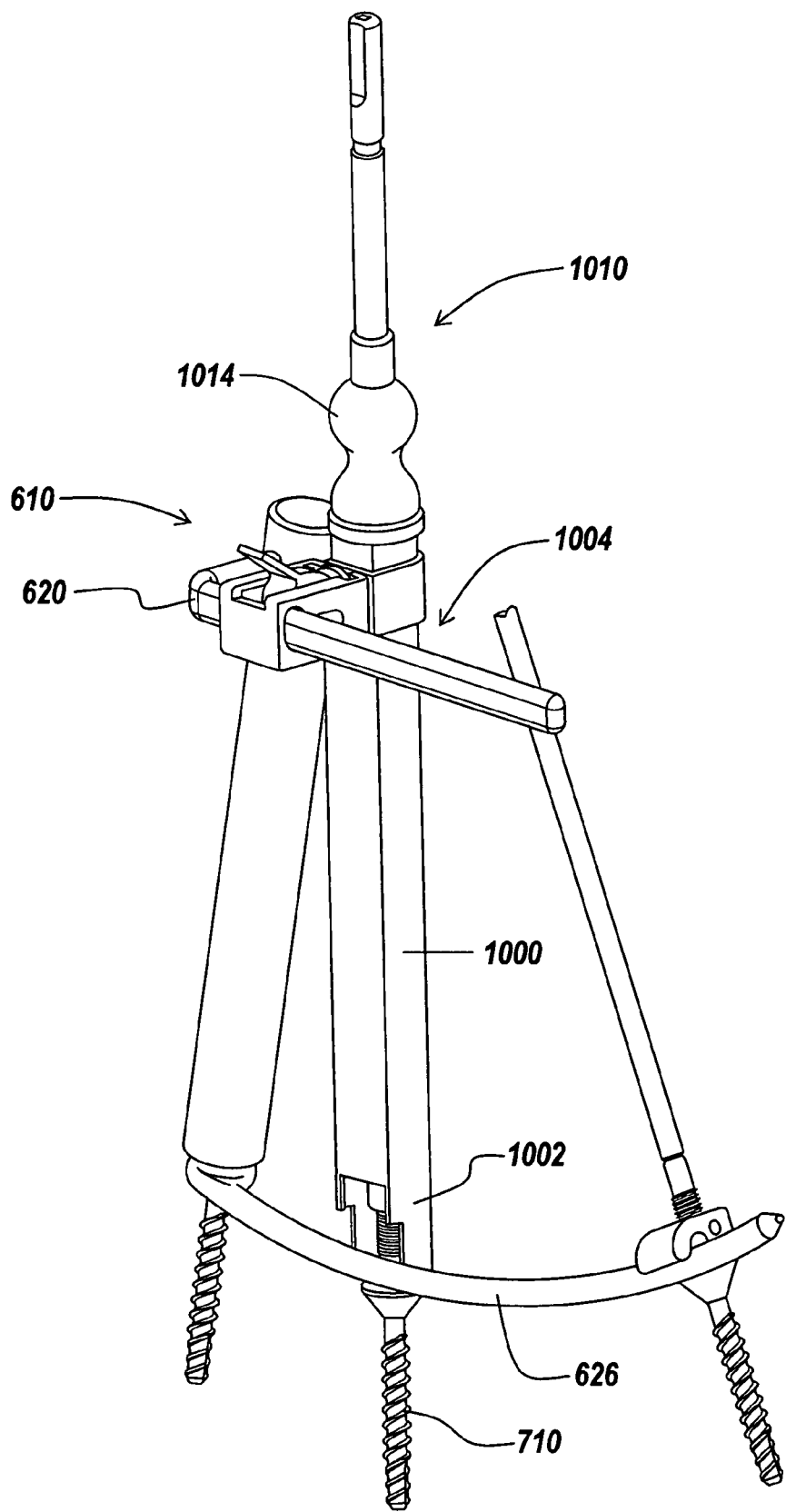

FIG. 10B illustrates the cannula 1000, with the attached vertebral body rotator head 1010, attached to the support arm 620 of the guide system 610 to anchor the position of the bone anchor 710. In this example, the handle 1012 has been removed from the vertebral body rotator head 1010.

In certain embodiments, the vertebral body rotator head 1010 may include a connection element 1014 that allows multiple vertebral body rotator heads 1010 to be connected and manipulated (i.e. rotated) together. An example of this can be seen in FIGS. 10C and 10D.

Figure 10C:
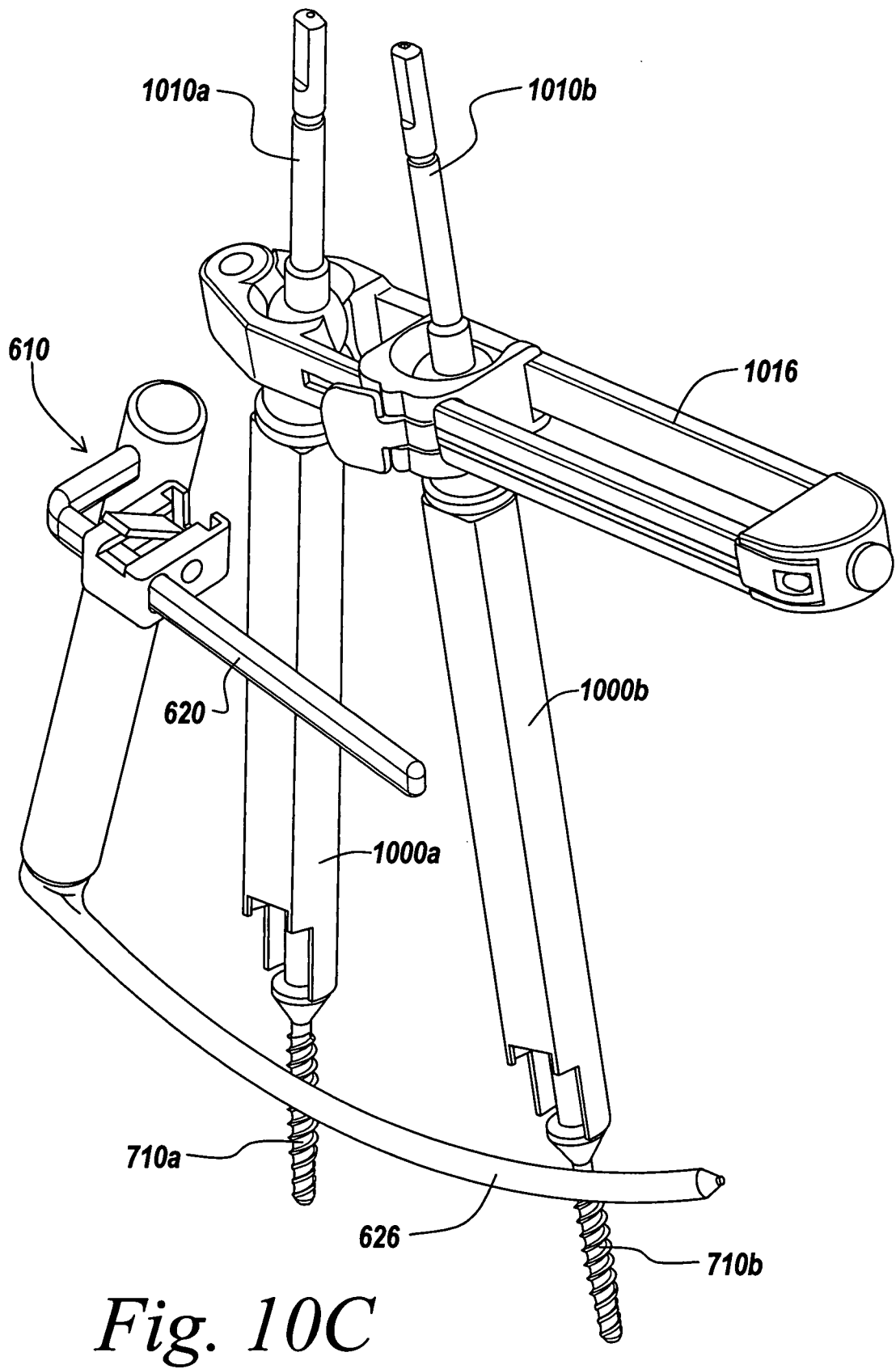

FIG. 10C illustrates one embodiment of vertebral body rotator heads 1010a, 1010b are attached to cannulae 1000a, 1000b. The vertebral body rotator heads 1010a, 1010b are connected together with a connector 1014. Once connected, the vertebral body rotator heads 1010a, 1010b may be used in unison to manipulate (i.e. rotate) the bone anchors 710a, 710b (and attached vertebra) engaged by the cannulae 1000a, 1000b.

Figure 10D:
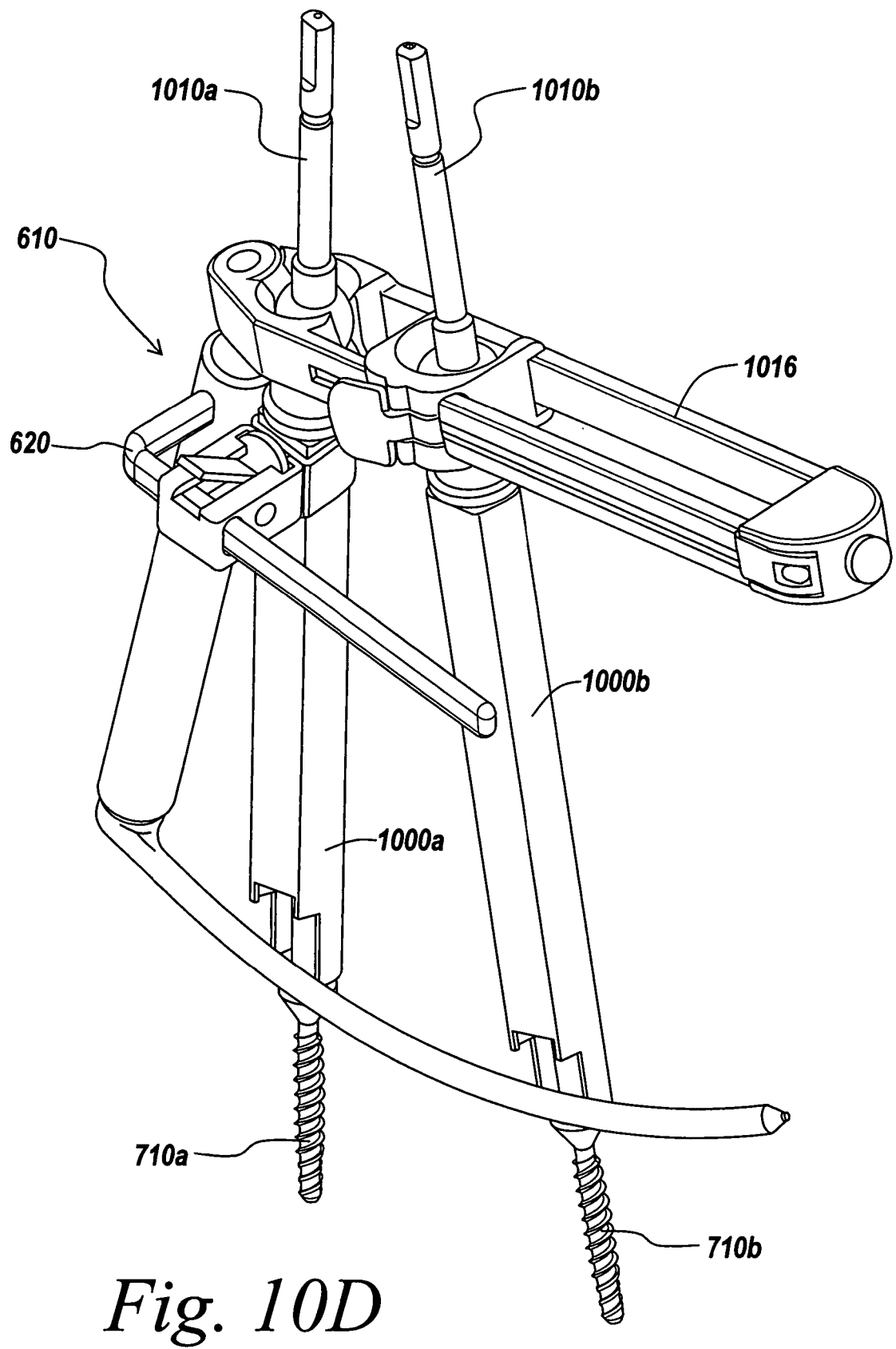

FIG. 10D illustrates the cannulae 1000a, 1000b, with the attached and connected vertebral body rotator heads 1010a, 1010b, attached to the support arm 620 of the guide system 610 to anchor the position of the bone anchors 710a, 710b.

Further discussion of vertebral body rotators can be found in related U.S. patent application Ser. No. 11/073,352, entitled "Instruments and Methods for Manipulation Vertebra," filed on Mar. 4, 2005

Although the examples of FIGS. 7-10 focused on cannulas, it should be understood that other insertion and manipulation instruments may be used to approximate the misaligned vertebra toward the inserted rod. Other instruments such as access ports, vertebral manipulators, and inserters may be used in for approximating.

It should be understood that any of the features or techniques described in relation to a specific embodiment may also be used in conjunction with any other embodiment. For example winching techniques can be used in conjunction with cannulas or other instruments. Other possible combinations or permutations will be apparent to one skilled in the art given the benefit of this disclosure.

Once, the vertebra has been approximated into a correct position, the bone anchor of the vertebra may then be connected to the rod (step 150 of FIG. 1). Various techniques can be used to connect the bone anchor in the approximated vertebra. For example, if a cannula or other insertion tool was used for implanting the bone anchor, a connector and locking mechanism may be inserted using the same cannula or insertion tool. A person skilled in the art will appreciate that a variety of other techniques can be used to couple a rod to the bone anchor. Moreover, the rod does not need to be directly attached to each anchor, and it can be indirectly attached to the anchors using, for example, a band clamp, or slotted or offset connectors. Once the rod is fully seated in the receiver head of each rod anchor system, a closure mechanism can be applied to each receiver head to retain the rod therein. Examples of suitable connectors and techniques for using them can be found in related applications DUQ-033, DUQ-036, and DUQ-037.

A person having ordinary skill in the art will appreciate that the aforementioned methods and devices for approximating bone anchors can be modified depending on the type of anchor being used, as well as the specific procedure being employed. Moreover, other methods and devices known in the art can be used in accordance with the present invention.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

While the instruments and methods disclosed herein have been particularly shown and described with reference to the exemplary embodiments thereof, those of ordinary skill in the art will understand that various changes may be made in the form and details herein without departing from the spirit and overall scope. Those of ordinary skill in the art will recognize or be able to ascertain many equivalents to the exemplary embodiments described specifically herein by using no more than routine experimentation. Such equivalents are intended to be encompassed by the overall scope and the appended claims.

The invention claimed is:

1. An instrument for approximating a misaligned bone anchor toward a spinal rod extending along a patient's spinal column, the instrument comprising:
    a first clamp configured to attach to a first location on the spinal rod;
    a second clamp configured to attach a second location on the spinal rod;
    a bone anchor engagement portion disposed between the first and second clamps and configured to engage the misaligned bone anchor that is laterally displaced from the spinal rod and misaligned from a location on the spinal rod between the first location and the second location;
    a first winch mechanism connecting the first clamp to the bone engagement portion, wherein the first winch mechanism adjusts a first distance between the first clamp and the bone anchor engagement portion; and
    a second winch mechanism connecting the second clamp to the bone engagement portion, wherein the second winch mechanism adjusts a second distance between the second clamp and the bone anchor engagement portion, wherein the first winch mechanism is actuated independently of the second winch mechanism,
    wherein the bone anchor engagement portion is adapted to move toward the spinal rod in a direction substantially perpendicular to a central axis of the patient's spinal column by adjusting the first distance and the second distance.

2. The instrument of claim 1, wherein at least one of the first winch mechanism and the second winch mechanism comprises a rack and pinion mechanism.

3. The instrument of claim 1, wherein at least one of the first winch mechanism and the second winch mechanism comprises a cable winch mechanism.

* * * * *